US012624998B2

(12) United States Patent     (10) Patent No.: US 12,624,998 B2

Ko et al.     (45) Date of Patent: May 12, 2026

(54) OPTICAL SENSING MODULE, SYSTEM AND METHOD FOR OPERATING OPTICAL SENSING SYSTEM

(71) Applicant: LITE-ON SINGAPORE PTE. LTD., Singapore (SG)

(72) Inventors: Lay-Thant Ko, Singapore (SG); Rui-Tao Zheng, Singapore (SG); Mon-Oo Win, Singapore (SG)

(73) Assignee: LITE-ON SINGAPORE PTE. LTD., Singapore (SG)

( * ) Notice: Subject to any disclaimer, the term of this patent is extended or adjusted under 35 U.S.C. 154(b) by 186 days.

(21) Appl. No.: 18/490,717

(22) Filed: Oct. 19, 2023

(65) Prior Publication Data

US 2024/0219235 A1     Jul. 4, 2024

(30) Foreign Application Priority Data

Dec. 30, 2022     (SG) ............................ 10202260647U
Jun. 1, 2023     (CN) ......................... 202310642578.6

(51) Int. Cl.
    *G01J 3/36*     (2006.01)
    *G01N 33/483*     (2006.01)
    (Continued)

(52) U.S. Cl.
    CPC ........... *G01J 3/36* (2013.01); *G01N 33/4833* (2013.01); *G01S 17/04* (2020.01); *G02B 1/002* (2013.01); *G02B 5/201* (2013.01); *G02B 5/286* (2013.01); *G02B 26/001* (2013.01); *H03F 1/223* (2013.01); *H03F 3/45237* (2013.01); *H03F 3/45475* (2013.01); *H03F 3/45748* (2013.01);
    (Continued)

(58) Field of Classification Search
None
See application file for complete search history.

(56) References Cited

U.S. PATENT DOCUMENTS 6,424,442 B1 * 7/2002 Gfeller .................. H04B 10/40
                                362/245
2012/0074322 A1 * 3/2012 Skurnik ............... G01J 1/4228
                                257/432

(Continued)

FOREIGN PATENT DOCUMENTS

JP     2016158144 A * 9/2016

*Primary Examiner* — Marcus H Taningco
(74) *Attorney, Agent, or Firm* — Li & Cai Intellectual Property Office

(57) ABSTRACT

The present disclosure relates to an optical sensing module, a system and a method for operating the optical sensing system. The optical sensing module includes a light emitter that emits a sensing light in a specific wavelength range and a photodiode unit. The photodiode unit includes a first photodiode used to sense a first wavelength light, a second photodiode used to sense a second wavelength light, and a third photodiode used to sense a third wavelength light. The optical sensing module implements a proximity sensor by operations of the second photodiode and the third photodiode, or a biometric sensor by operations of the first photodiode, the second photodiode, and the third photodiode. The photodiode unit receives a reflected light from an object to be detected so as to determine if the object is proximal, and then determine whether or not the proximal object is human skin.

19 Claims, 6 Drawing Sheets

(51) Int. Cl.

| | | |
|---|---|---|
| *G01S 17/04* | (2020.01) | |
| *G02B 1/00* | (2006.01) | |
| *G02B 5/20* | (2006.01) | |
| *G02B 5/28* | (2006.01) | |
| *G02B 26/00* | (2006.01) | |
| *H03F 1/22* | (2006.01) | |
| *H03F 3/45* | (2006.01) | |
| *H03F 3/68* | (2006.01) | |
| *G01J 3/28* | (2006.01) | |
| *G01N 21/3563* | (2014.01) | |

(52) U.S. Cl.
CPC ........ *H03F 3/68* (2013.01); *G01J 2003/2806* (2013.01); *G01N 2021/3568* (2013.01); *G01N 2201/125* (2013.01); *G02B 2207/101* (2013.01); *H03F 2200/165* (2013.01); *H03F 2200/375* (2013.01); *H03F 2203/45151* (2013.01); *H03F 2203/45212* (2013.01)

(56) References Cited

U.S. PATENT DOCUMENTS

| 2017/0172462 A1* | 6/2017 | Alghazi | ................... | A45B 3/00 |
|---|---|---|---|---|
| 2017/0254703 A1* | 9/2017 | Purohit | ................. | G01J 5/0025 |
| 2018/0360326 A1* | 12/2018 | Lee | ....................... | G06F 3/0346 |
| 2020/0056771 A1* | 2/2020 | Cho | ....................... | G06F 1/3215 |
| 2020/0343295 A1* | 10/2020 | Kang | ................... | H04N 25/131 |
| 2021/0044684 A1* | 2/2021 | Baek | ..................... | H01Q 1/243 |
| 2021/0200366 A1* | 7/2021 | Bok | ....................... | G06V 10/17 |

* cited by examiner

| wavelength | Photodiode | light emitter power | overall sensitivity |
|---|---|---|---|
| 890nm | 0. 9 | 0. 75 | 0. 675 |
| 970nm | 0. 85 | 1 | 0. 85 |
| 1050nm | 0. 24 | 0. 5 | 0. 12 |

FIG. 5

OPTICAL SENSING MODULE, SYSTEM AND METHOD FOR OPERATING OPTICAL SENSING SYSTEM

CROSS-REFERENCE TO RELATED PATENT APPLICATION

This application claims the benefit of priorities to Singapore Provisional Patent Application No. 10202260647U, filed on Dec. 30, 2022, and China Patent Application No. 202310642578.6, filed on Jun. 1, 2023 in People's Republic of China. The entire content of the above identified applications are incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to an optical sensing technology, and more particularly to an optical sensing module that uses characteristics of multiple infrared wavelength bands to perform proximity detection and skin detection, a system and a method for operating the optical sensing system.

BACKGROUND OF THE DISCLOSURE

The conventional skin detection technology uses red (R), green (G) and blue (B) light in visible light bands to calculate among the sensing values of different color channels in the red, green and blue (RGB) color space. The reflectance ratio or the reflectance of different colors is compared, and whether human skin is detected is judged according to the reflection characteristics of the skin to these lights. Therefore, a sensor for skin detection requires a visible light source. However, each time when the sensor starts to measure the reflected lights, a user may be distracted by blinking lights, and certain power consumption is required to drive the three light emitters.

Furthermore, in the conventional technology, in addition to using a red light, a green light, or an infrared light to detect changes of the human skin, the lights can also be used to measure a heart rate. However, the disadvantage of the above method is that two light emitters are required and the light sources are required to be continuously switched-on since a long period of time is needed for collecting data. Similarly, the blinking visible lights still cause distraction, and a certain power consumption for driving at least two light emitters is required.

In one further conventional technology, a short-wave infrared light (SWIR) emitter having a wavelength range of from 0.9 μm to 1.7 μm, or from 0.7 μm to 2.5 μm is used as a light emitter and a sensor for detecting human skin. However, the SWIR emitter and the sensor cannot be manufactured by using a silicon wafer manufacturing technology and require an additional manufacturing process to assemble the components, thus resulting in additional costs and material consumption.

SUMMARY OF THE DISCLOSURE

In response to the above-referenced technical inadequacies of the conventional technologies that utilize a visible light to sense human skin and use a short-wave infrared light as a light source, the present disclosure provides an optical sensing module, an optical sensing system and a method for operating the optical sensing system for improving the above-referenced issues.

The optical sensing module mainly includes a light emitter that is used to emit a sensing light with a spectrum covering an infrared wavelength range and a photodiode unit that includes a first photodiode, a second photodiode, and a third photodiode. The first photodiode is used to sense a first wavelength light and is connected with a first signal converter. The second photodiode is used to sense a second wavelength light and is connected with a second signal converter. The third photodiode is used to sense a third wavelength light and is connected with a third signal converter.

In an aspect of the present disclosure, the optical sensing module implements a proximity sensor by operations of the second photodiode and the third photodiode; and the optical sensing module implements a biometric sensor by operations of the first photodiode, the second photodiode, and the third photodiode.

Furthermore, the first photodiode, the second photodiode, and the third photodiode are silicon photodiodes that include filter materials for various wavelength bands. The filter materials allow the first photodiode, the second photodiode, and the third photodiode to respectively sense lights in wavelength ranges of from 870 nm to 910 nm, from 950 nm to 990 nm, and from 1030 nm to 1070 nm.

Moreover, a sensing area of at least one of the first photodiode and the third photodiode is larger than the sensing area of the second photodiode, so that variations in the optical sensing module can be reduced.

Preferably, the light emitter is a wide spectrum infrared light emitter to emit the sensing light with the spectrum covering a wavelength from 800 nm to 1100 nm. In particular, a wavelength of the first wavelength light is between 870 nm and 910 nm, a wavelength of the second wavelength light is between 950 nm and 990 nm, and a wavelength of the third wavelength light is between 1030 nm and 1070 nm.

Furthermore, the first signal converter, the second signal converter, and the third signal converter respectively convert sensing values generated by the first photodiode, the second photodiode, and the third photodiode into a first digital signal, a second digital signal, and a third digital signal; and the photodiode unit further includes a signal-regulating circuit that drives the first signal converter, the second signal converter, and the third signal converter to respectively adopt different gains so as to reduce variations in the optical sensing module.

In addition, when a sum of the second digital signal and the third digital signal is larger than or equal to a threshold, the proximity sensor determines that an object is proximal to the optical sensing module.

In one aspect, based on characteristics of a skin reflecting the lights in various wavelength bands, when both the first digital signal generated by the first signal converter and the third digital signal generated by the third signal converter are larger than the second digital signal generated by the second signal converter, the biometric sensor determines that a surface of an object is human skin.

In another aspect, based on a biometric threshold, when a magnitude of the first digital signal is 1.1 to 2 times a magnitude of the second digital signal, and a magnitude of the third digital signal is 1.1 to 2 times the magnitude of the second digital signal, a proximal object is determined to be human skin.

Further, in one aspect of the optical sensing system, the optical sensing system essentially includes a control unit and the optical sensing module. The optical sensing system includes the light emitter and the photodiode unit. The control unit drives the light emitter to emit a sensing light with a spectrum covering an infrared wavelength range and processes a sensing value generated by the photodiode unit when sensing the light reflected by an object.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which:

FIG. 5 shows data of sensitivity of components of an optical sensor for lights of various wavelength bands.

DETAILED DESCRIPTION OF THE EXEMPLARY EMBODIMENTS

Figure 1:
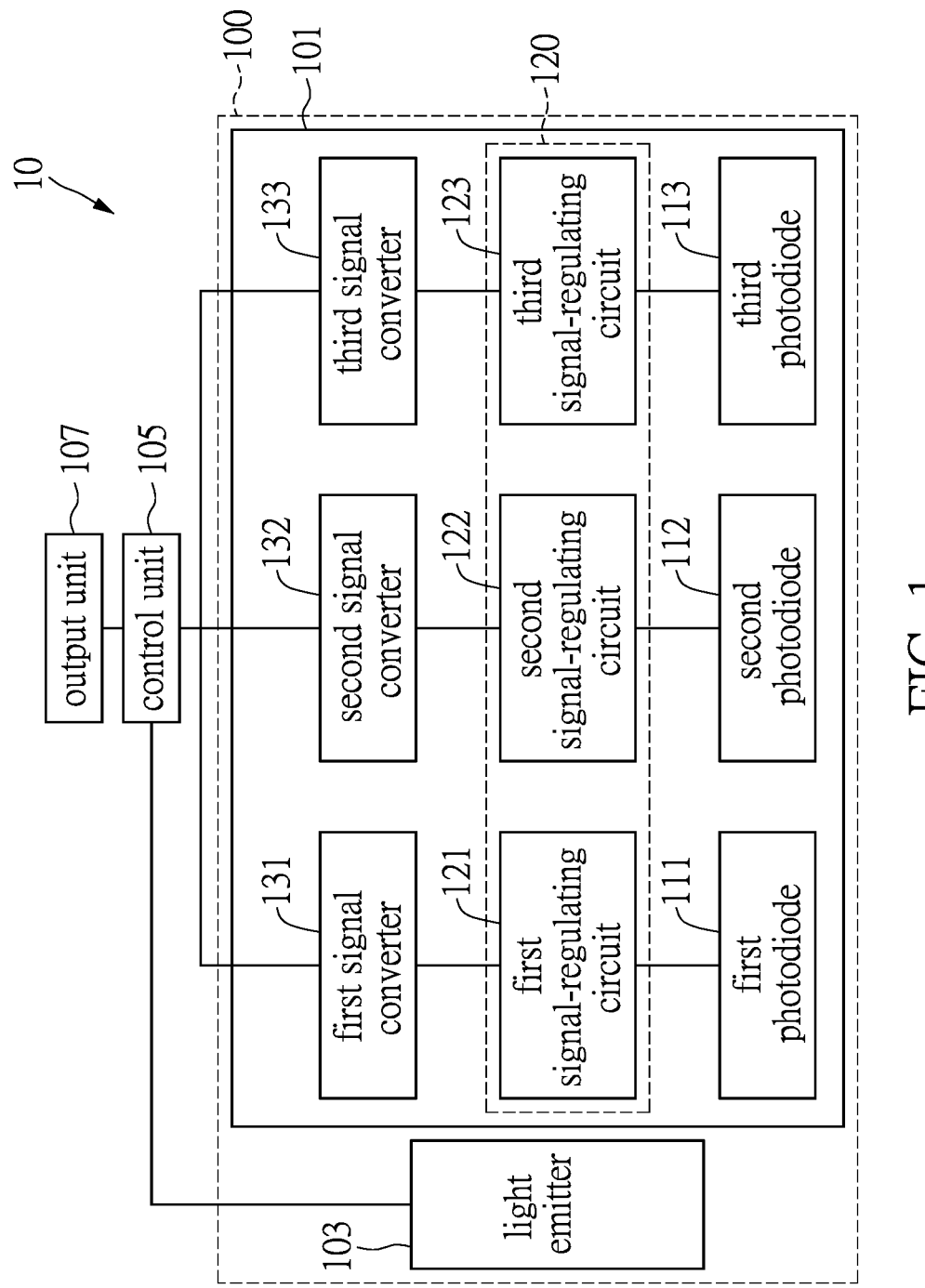
FIG. 1 is a schematic diagram showing a circuit system of an optical sensing module and optical sensing system according to one embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a," "an" and "the" includes plural reference, and the meaning of "in" includes "in" and "on." Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first," "second" or "third" can be used to describe various components, signals or the like, which are for distinguishing one component/signal from another one only, and are not intended to, nor should be construed to impose any substantive limitations on the components, signals or the like.

The present disclosure relates to an optical sensing module, an optical sensing system and a method for operating the optical sensing system. A light source of the optical sensing module is neither a light emitter that emits light in a visible light wavelength range, nor a light emitter that emits the short-wave infrared light for detecting human skin in the conventional technology. According to one embodiment of the present disclosure, the light emitter of the optical sensing module uses a single wide spectrum infrared light as a light source. The light emitter can be manufactured by using a silicon wafer manufacturing process for reducing material cost and manufacturing cost. In addition, the power consumption can also be reduced since only one light emitter is required.

Reference is made to FIG. 1, which is a schematic diagram illustrating a circuit system that applies an optical sensing module according to one embodiment of the present disclosure.

The circuit system that implements an optical sensing system 10 includes a control unit 105 and an optical sensing module 100. The optical sensing module 100 mainly includes main components such as a photodiode unit 101 and a light emitter 103. The optical sensing module 100 implements a proximity sensor and a biometric sensor. The control unit 105 is electrically connected with the photodiode unit 101 and the light emitter 103. The control unit 105 is used to control operations of the whole device. For example, the control unit 105 drives the light emitter 103 to emit a sensing light and then processes a sensing value generated by the photodiode unit 101 that senses the light reflected by a specific object. The circuit system further includes an output unit 107 that is electrically connected with the control unit 105 and outputs a sensing result obtained from the control unit 105, so that other applications can be accomplished by utilizing the sensing result.

According to one embodiment of the optical sensing module 100, one of the main components of the optical sensing module 100 is the light emitter 103 that can use the wide spectrum infrared light emitter as a light source, and the wavelength range of the sensing light is between 800 nm and 1100 nm.

The other main component of the optical sensing module 100 is the photodiode unit 101. In one embodiment of the present disclosure, a photodiode of the photodiode unit 101 is an optical sensing component manufactured by a silicon manufacturing process. The photodiode unit 101 includes a first photodiode 111 that is used to sense a first wavelength light. Preferably, the wavelength of the first wavelength light is between 870 nm and 910 nm. The first photodiode 111 is connected with a first signal converter 131 that performs analog-to-digital conversion for converting a sensing value of the first photodiode 111 into a first digital signal. Furthermore, according to requirements of a practical application, a first signal-regulating circuit 121 can be disposed between the first photodiode 111 and the first signal converter 131.

In one embodiment of the present disclosure, the first photodiode 111, the second photodiode 112, and the third photodiode 113 are the silicon photodiodes manufactured by a silicon manufacturing process. In the silicon manufacturing process, various filter materials for passing through the light with different wavelength bands are used for allowing the first photodiode 111, the second photodiode 112, and the third photodiode 113 to have higher sensitivities in the wavelength ranges of from 870 nm to 910 nm, from 950 nm to 990 nm, and from 1030 nm to 1070 nm, respectively. Therefore, the photodiode unit 101 can sense lights in the wavelength ranges of from 870 nm to 910 nm, from 950 nm to 990 nm, and from 1030 nm to 1070 nm, respectively.

Furthermore, the second photodiode 112 of the photodiode unit 101 is used to sense a second wavelength light. Preferably, a wavelength of the second wavelength light can be between 950 nm and 990 nm. The second photodiode 112 is connected with a second signal converter 132 that performs analog-to-digital conversion to convert the sensing value of the second photodiode 112 into a second digital signal. Similarly, in requirements of practical application, a second signal-regulating circuit 122 is provided between the second photodiode 112 and the second signal converter 132.

The photodiode unit 101 further includes the third photodiode 113 that is used to sense a third wavelength light. Preferably, a wavelength of the third wavelength light is between 1030 nm and 1070 nm. The third photodiode 113 is connected with a third signal converter 133 that performs analog-to-digital conversion for converting the sensing value generated by the third photodiode 113 into a third digital signal. Furthermore, a third signal-regulating circuit 123 is disposed between the third photodiode 113 and the third signal converter 133.

According to certain embodiments of the present disclosure, in the optical sensing module 100, the signal converter corresponding to each of the photodiodes is such as an analog-to-digital converter (ADC) that is used to convert the sensing value generated by the photodiodes (e.g., intensity of light reflected by a specific object) into digital signals. The sensing values that are output may be diverse since the photodiodes have different sensitivities to lights of different wavelength bands. In one embodiment of the present disclosure, the sensitivity of the photodiode to the light in the wavelength band of from 1030 nm to 1070 nm is only 24% of the sensitivity of the photodiode to the light in the wavelength band of from 950 nm to 990 nm. For reducing variations among the sensing values generated by the photodiodes of the optical sensing module 100, a signal-regulating circuit 120 is disposed between the first, second, and third photodiodes 111, 112, and 113 and the corresponding signal converters 131, 132, and 133. Practically, the signal-regulating circuit 120 can be implemented by a first signal-regulating circuit 121, a second signal-regulating circuit 122, and a third signal-regulating circuit 123 corresponding to the abovementioned photodiodes and signal converters. The first signal-regulating circuit 121, the second signal-regulating circuit 122, and the third signal-regulating circuit 123 correspondingly apply different gains to the first signal converter 131, the second signal converter 132, and the third signal converter 133, so that the variations in the optical sensing module 100 can be reduced.

It should be noted that, in the present embodiment, the optical sensing module 100 includes multiple photodiodes including the first photodiode 111, the second photodiode 112, and the third photodiode 113. The optical sensing module 100 uses the three different photodiodes to sense the lights in three different wavelength bands respectively ranging from 870 nm to 910 nm, from 950 nm to 990 nm, and from 1030 nm to 1070 nm. Furthermore, based on the various optical characteristics of the photodiodes in the three different wavelength bands of infrared lights, the second photodiode 112, the third photodiode 113, and optionally the relevant circuits such as the second signal-regulating circuit 122, the third signal-regulating circuit 123, the second signal converter 132, and the third signal converter 133 can operate as a proximity sensor. Similarly, the first photodiode 111, the second photodiode 112, the third photodiode 113, and optionally the relevant circuits can operate as a biometric sensor. The optical sensing module 100 can function independently as the proximity sensor or the biometric sensor.

According to the above-described embodiments, the optical sensing module 100 includes multiple photodiodes that are configured to respectively sense lights of different wavelength bands. Accordingly, the biometric sensor can be implemented by applying the optical characteristics of the infrared lights in different wavelength bands to the photodiodes. One of the functions of the biometric sensor is to sense human skin.

Figure 2:
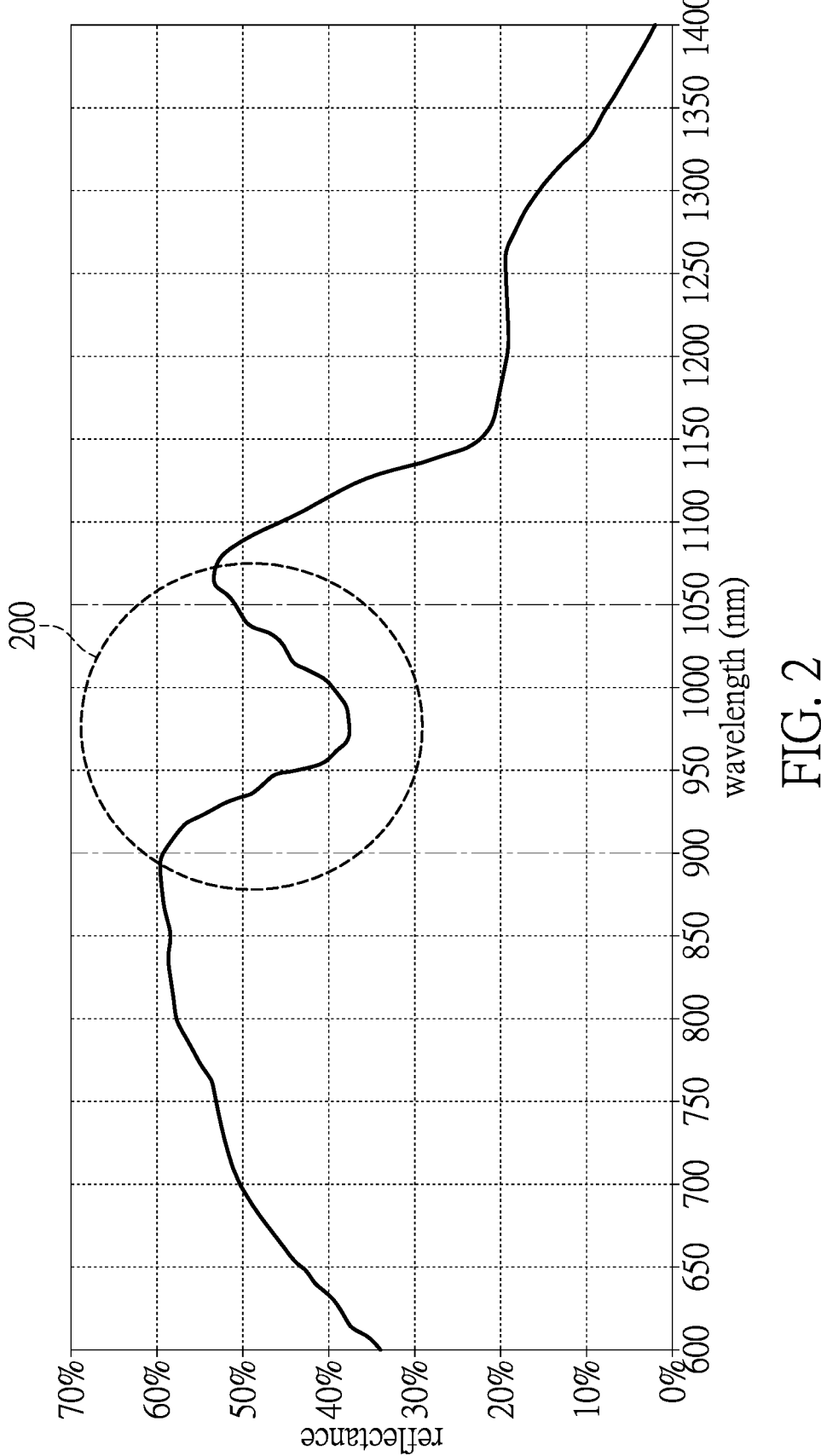
FIG. 2 is a schematic diagram showing light reflective characteristics of human skin in different wavelength bands.

Reference is made to FIG. 2, which is a schematic diagram illustrating light reflecting characteristics of human skin in different wavelength bands.

The curve diagram shown in FIG. 2 illustrates changes of the reflectance of human skin in different wavelength bands (e.g., wavelength ranges of from 600 nm to 1400 nm) to. In particular, a human skin reflective characteristic region 200 is marked in the curve diagram, and the human skin reflective characteristic region 200 shows that the human skin reflectance with respect to a detection wavelength range of from 900 nm to 1100 nm (within the wavelength coverage of the first photodiode 111, the second photodiode 112, and the third photodiode 113) has a significantly lower curve that forms a "V"-shaped curve. In other words, the human skin reflective characteristic region 200 indicates that the human skin has a lower absorption rate to the lights in the wavelength bands of from 870 nm to 910 nm and from 1030 nm to 1070 nm, and has a higher absorption rate to the lights in the wavelength bands of from 950 nm to 990 nm.

The characteristics shown in the curve diagram indicates that, compared to the lights in the wavelength ranges of from 870 nm to 910 nm and from 1030 nm to 1070 nm, human skin has a relatively low reflectance (or relatively high absorption rate) of the light in the wavelength range of from 950 nm to 990 nm. Therefore, when the photodiode unit 101 of the optical sensing module 100 of the present disclosure adopts the photodiodes (111, 112, 113) that are used to respectively sense the lights in the wavelength ranges of from 870 nm to 910 nm, from 950 nm to 990 nm, and from 1030 nm to 1070 nm, the optical sensing module 100 can effectively sense human skin and exclude the cases in which human skin is not sensed.

Figure 3:
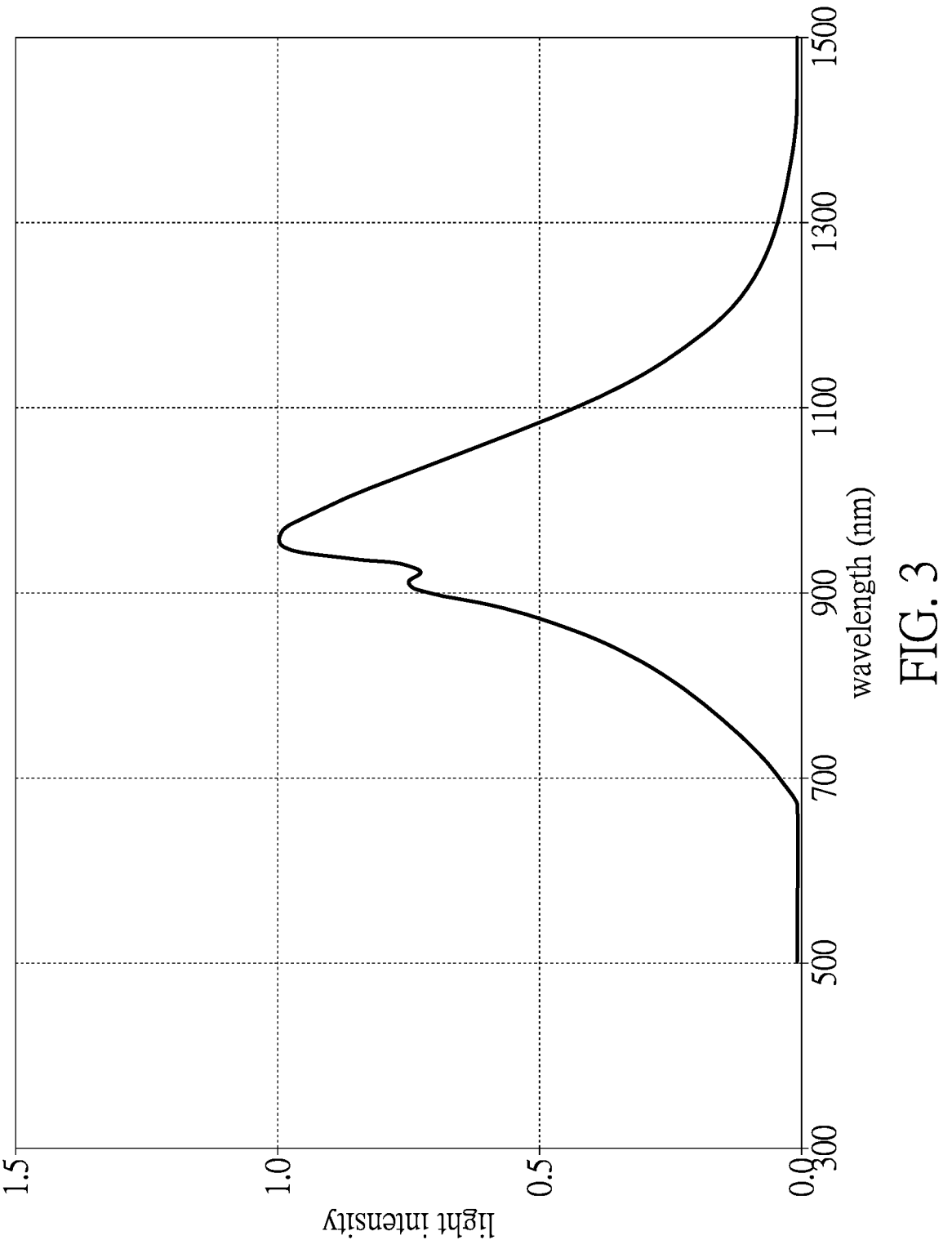
FIG. 3 is a schematic diagram showing an intensity distribution of a wide spectrum infrared light.

Reference is made to FIG. 3, which shows an intensity distribution of the wide spectrum infrared light, and the intensity distribution acts as a reference for the optical sensing module that adopts the wide spectrum infrared light to be a light source of the light emitter 103. The wavelength band of the wide spectrum infrared light is approximately between 700 nm and 1300 nm and covers the abovementioned three wavelength bands respectively ranging from 870 nm to 910 nm, from 950 nm to 990 nm, and from 1030 nm to 1070 nm. Thus, by referring to the human skin reflective characteristic region 200 with the spectrum covering the wavelength range between 900 nm and 1100 nm of FIG. 2, the wide spectrum infrared light is able to be the light source of the light emitter 103 for performing human skin detection and proximity detection.

However, human skin has a variety of skin tones since different people have different skin tones, and different people of different races have further different skin tones.

Figure 4:
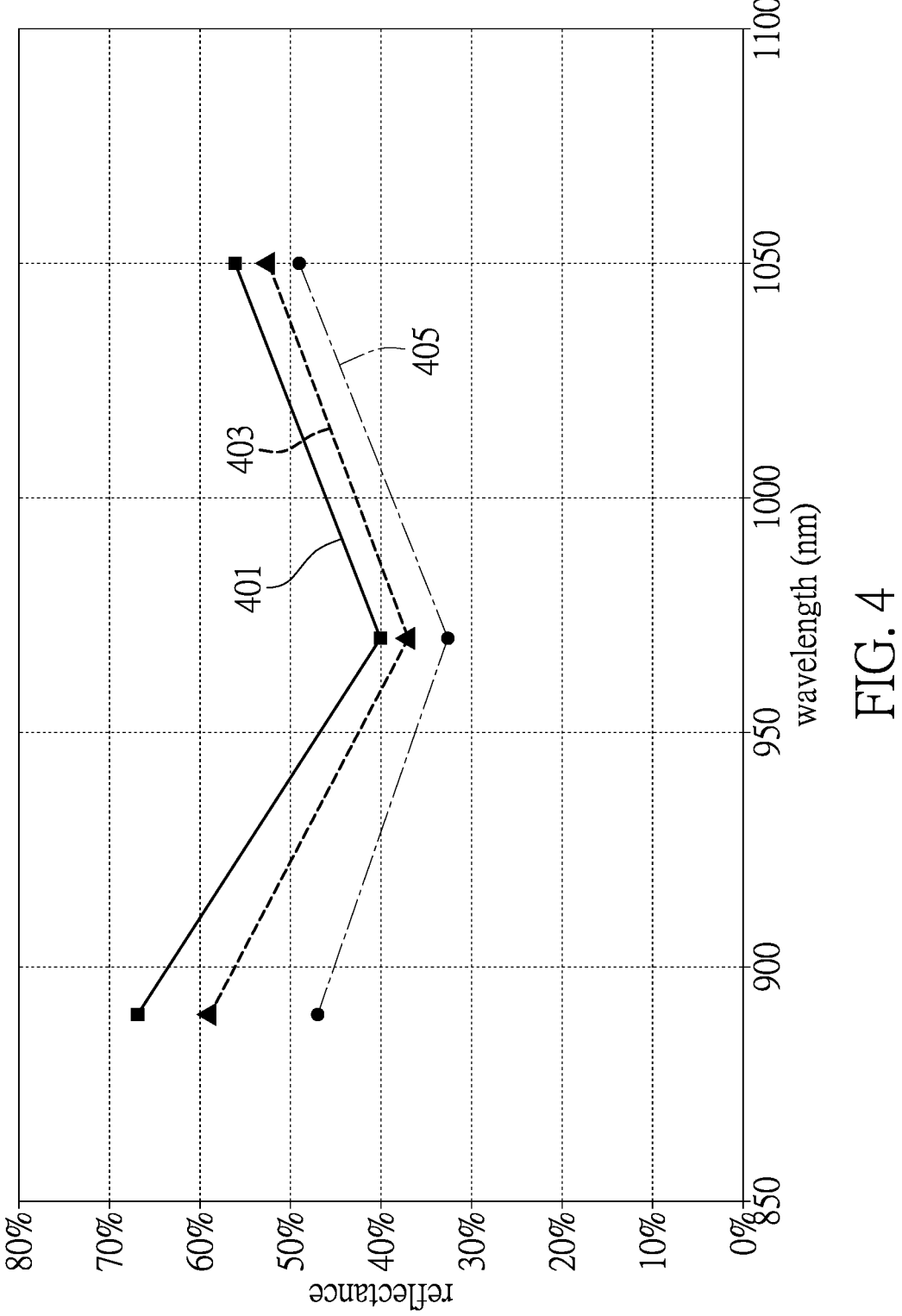
FIG. 4 is a schematic diagram showing reflective characteristics among different skin tones in infrared wavelength bands.

Reference is made to FIG. 4, which is a diagram illustrating the reflective characteristics among different skin tones in infrared wavelength bands.

The skin tones illustrated in FIG. 4 can be categorized into three types of skin tones including a light tone, a medium tone, and a dark tone. When the reflectance for each of skin tones is measured, the measurement result indicates that the reflective characteristics of a light skin tone 401, a medium skin tone 403, and a dark skin tone 405 in the wavelength bands of 890 nm, 970 nm, and 1050 nm have similar reflective characteristic trends depicted in the human skin reflective characteristic region 200 of FIG. 2. That is, the various skin tones have relatively low reflectance around the wavelength band of 970 nm. This means that the optical sensing module 100 of the present disclosure is suitable for sensing the skins with different skin tones. In addition, as shown in FIG. 4, compared to the reflectance in 970 nm and 1050 nm, the reflectance of dark skin tone 405 in 890 nm considerably deviates from the reflectance of light skin tone 401 and medium skin tone 403 (e.g., more than 10%).

Next, FIG. 5 is a table illustrating the sensitivity data for each of components of the optical sensing module 100 in various wavelength bands. The table shows that the sensing values 0.9, 0.85, and 0.24 are the normalized sensing values of the photodiodes (111, 112, 113) to the light in the wavelength band of around 890 nm, 970 nm and 1050 nm; and the sensitivity values 0.75, 1, and 0.5 are the normalized power values of the lights emitted by the light emitter 103 in the wavelength band of around 890 nm, 970 nm and 1050 nm. Further, for the optical sensing module 100 as a whole that includes the photodiode unit 101 and the light emitter 103, the sensitivity values 0.675, 0.85, and 0.12 are the normalized performance values of the optical sensing module 100 of the lights in the wavelength band of around 890 nm, 970 nm and 1050 nm. In addition, since the light emitter 103 and the photodiode (111, 112, 113) can be made by different materials, manufacturing methods, or have different structures, the power and sensitivity of the light emitter 103 may be different and the sensitivity data for the optical sensing module 100 is not limited to the data as shown in FIG. 5.

According to the above data, the circuit components such as the photodiode 111 in the optical sensing module 100 have different sensitivities to the corresponding wavelength bands, thus may cause measurement error when the optical sensing module 100 is in operation. Therefore, when the sensing value is converted to the digital signals, certain adequate gain compensation can be applied for enhancing accuracy of sensing.

According to one embodiment of the present disclosure, in the circuit system shown in FIG. 1, the first signal converter 131, the second signal converter 132, and the third signal converter 133 respectively convert the sensing values generated by the first photodiode 111, the second photodiode 112, and the third photodiode 113 into the first digital signal, the second digital signal, and the third digital signal. At this time, the signal-regulating circuit 120 (i.e., the first signal-regulating circuit 121, the second signal-regulating circuit 122, and the third signal-regulating circuit 123) of the optical sensing module 100 drives the first signal converter 131, the second signal converter 132, and the third signal converter 133 to respectively apply different gains for reducing the variations in the optical sensing module 100.

In one exemplary example, according to the data shown in FIG. 5, the first photodiode 111 is used to sense the lights in the wavelength band of around 890 nm, and the sensing value can be converted into digital signals by the first signal converter 131 that can be applied with gain compensation. For example, as shown in FIG. 5, the gain value applied to the first signal converter 131 can be 1.26 (i.e., 0.85/0.675=1.26). Furthermore, referring to FIG. 5, the third photodiode 113 is used to sense the lights in the wavelength band of around 1050 nm, and the sensing value can be converted into digital signals by the third signal converter 133 that can be applied with a gain value of 7.08 (i.e., 0.85/0.12=7.08). Thus, the digital signals that are finally obtained with the gain compensations can gain a consistent level with the digital signals converted from the sensing value generated by the second photodiode 112 that is used to sense the lights in the wavelength band of around 970 nm, thereby balancing the variations caused by the various sensitivities of the components of the optical sensing module 100. Furthermore, since the light emitter 103 and the photodiodes (111, 112, 113) can be made by different materials, different manufacturing processes, or have different structures, the sensitivity values of the optical sensing module 100 are not limited to the values as shown in FIG. 5, and the above-mentioned gain values for gain compensation are only exemplarily shown.

According to one further embodiment of the present disclosure, for effectively balancing the variations in the components of the optical sensing module 100, the variations of the sensing values of the photodiodes to the lights in the different wavelength bands should be calibrated. For example, a sensing area of at least one of the first photodiode 111 that is used to sense the lights in the wavelength band between 870 nm and 910 nm and the third photodiode 113 that is used to sense the lights in the wavelength band between 1030 nm and 1070 nm is larger than the sensing area of the second photodiode 112 that is used to sense the lights in the wavelength band between 950 nm and 990 nm. The photodiode having a larger sensing area can obtain more sensing values and the consistent sensitivities of the photodiodes can reduce the variations in the optical sensing module 100. For example, the variations of the sensitivities of the photodiodes can be effectively reduced when a surface area of each of the photodiodes used to respectively sense the lights in the wavelength band ranging from 870 nm to 910 nm and from 1030 nm to 1070 nm is designed to have approximately twice the surface area of the photodiode that is used to sense the lights in the wavelength band ranging from 950 nm to 990 nm.

Figure 6:
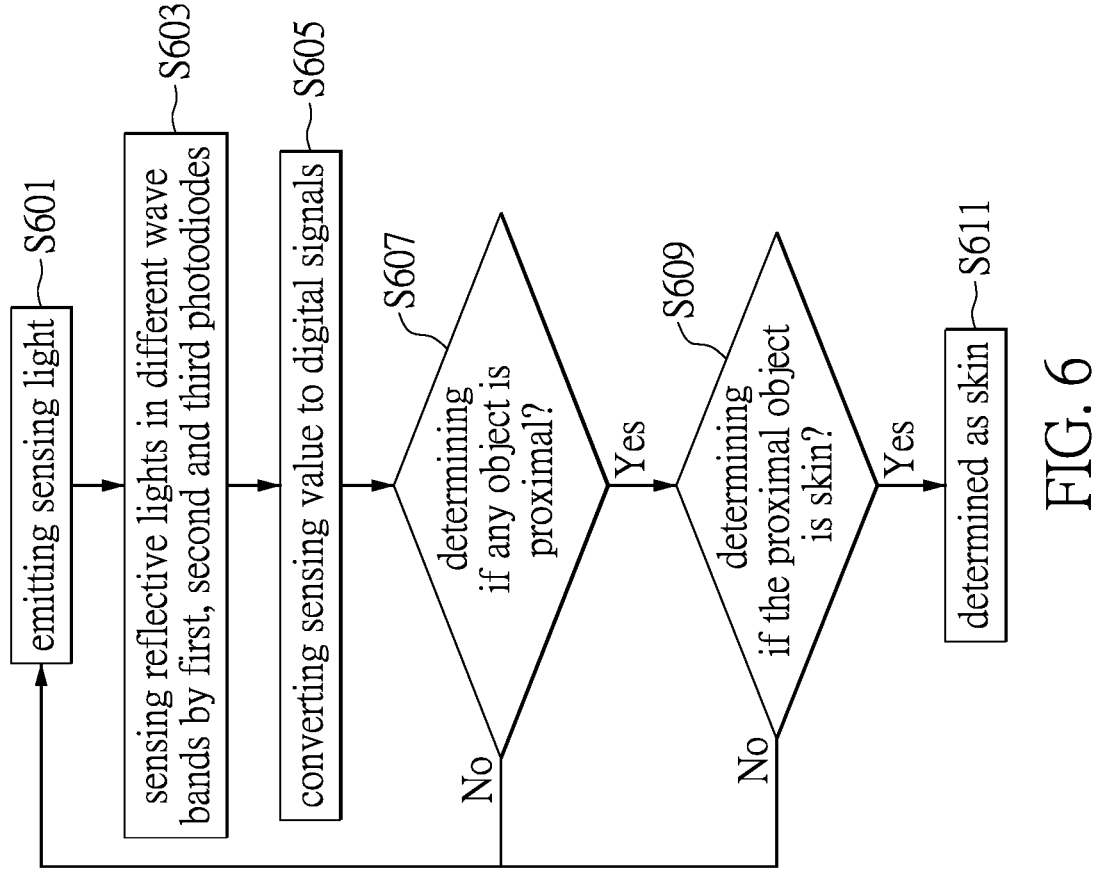
FIG. 6 is a flowchart illustrating a method for operating an optical sensing system according to one embodiment of the present disclosure.

According to the embodiment of the optical sensing module 100, the optical sensing module 100 provides a mechanism for balancing the variations caused by the components of the optical sensing module 100, so as to perform biometric identification that is mainly for detecting human skin. Reference is made to FIG. 6, which is a flowchart illustrating a method for operating the optical sensing system 10 having the optical sensing module 100. The method can be performed in a sensing device having the optical sensing module 100.

Firstly, the control unit 105 drives the light emitter 103 of the optical sensing module 100 to emit a sensing light to an object to be detected. It should be noted that, the wavelength band (e.g., between 800 nm and 1100 nm) of the sensing light at least covers three ranges of wavelength bands such as the ranges of from 870 nm to 910 nm, from 950 nm to 990 nm, and from 1030 nm to 1070 nm (step S601).

The sensing light is then reflected by the object to be detected. The first photodiode 111, the second photodiode 112, and the third photodiode 113 are configured to sense reflected light in the three different wavelength bands. According to the abovementioned embodiments of the present disclosure, the sensing values of the reflected lights in the wavelength bands ranging from 870 nm to 910 nm, from 950 nm to 990 nm, and from 1030 nm to 1070 nm can be obtained (step S603).

Afterwards, the corresponding first signal converter 131, the second signal converter 132, and the third signal converter 133 are used to convert the sensing values into a first digital signal, a second digital signal, and a third digital signal (step S605). Then, as described in the abovementioned embodiments, different gain compensations are applied to the digital signals with respect to the signal converters (131, 132, and 133).

Afterwards, the second digital signal, the third digital signal, and a predetermined proximity threshold are referred to for determining whether or not any object is proximal (step S607). When a sum of the second digital signal and the third digital signal is larger than or equal to the proximity threshold, the proximity sensor determines that the object to be detected is proximal to the optical sensing module 100 (determined as "yes"), and step S609 will be executed. If the proximity sensor does not detect any proximal object (determined as "no"), the process goes back to step S601 for repeating the aforementioned steps. It is worth noting that based on the characteristics curves shown in FIG. 4, compared to the wavelength bands of 970 nm and 1050 nm, the reflectance of the dark skin tone 405 in the wavelength band of 890 nm has larger deviation than both the reflectance of the light skin tone 401 and the reflectance of the medium skin tone 403 in the wavelength band of 890 nm (e.g., more than 10%). Therefore, such as in step S607, the first digital signal is not included for calculating a sum of the signals. Further, when determining the proximity threshold, it is unnecessary to take the first digital signal into consideration. Therefore, the method, e.g., step S607, can more accurately determine whether or not any object is proximal.

After the determination of the proximity, the process goes on determining whether or not a surface of the object is human skin by the first digital signal, the second digital signal and the third digital signal. That is, the sensing value (i.e., the digital signals) is compared with the biometric threshold set by the system so as to determine whether or not the proximal object is skin (step S609). If the sensing value matches with the biometric threshold (determined as "yes"), it is determined that the object is human skin (step S611). Otherwise, if the sensing value does not match with the biometric threshold, the process goes back to step S601 for repeating the abovementioned steps.

In one of the embodiments of the present disclosure, in the step of determining whether or not human skin is detected according to the characteristics of the lights sensed by the photodiodes in the different wavelength bands, when both the first digital signal generated by the first signal converter 131 and the third digital signal generated by the third signal converter 133 are larger than the second digital signal generated by the second signal converter 132, it is determined that the sensing value is consistent with the feature of a "V"-shaped curve (as shown in FIG. 2), indicating the changes of reflectance of lights to human skin in different wavelength bands. Accordingly, the biometric sensor can be used to determine whether or not the object to be detected is human skin.

According to one further embodiment of the present disclosure, another biometric threshold is determined based on the sensing characteristics of the photodiode for lights in different wavelength bands. Specifically, when a magnitude of the first digital signal is 1.1 to 2 times a magnitude of the second digital signal, and a magnitude of the third digital signal is 1.1 to 2 times the magnitude of the second digital signal, the object to be detected is determined as human skin.

According to the above embodiments of the optical sensing module, the optical sensing system and the method for operating the optical sensing system of the present disclosure, one of the main objectives is to implement a skin sensor that includes three photodiodes. Specifically, two of the photodiodes implement a proximity sensor that can be firstly driven to conduct proximity sensing. When an object is determined to be proximal, the three photodiodes are then driven to conduct skin detection. The abovementioned two-phase detection can reduce unnecessary signal transmission and processing for saving power consumption by controlling the number of the photodiodes to be driven. According to the above embodiments, human skin generally has a higher absorption rate for the lights in the wavelength band ranging from 950 nm to 990 nm, and a higher reflectance for the lights in the wavelength band ranging from 870 nm to 910 nm and from 1030 nm to 1070 nm. Accordingly, by determining whether or not any "V"-shaped curve is observed in a reflectance distribution diagram, it can be determined whether human skin is detected.

The foregoing description of the exemplary embodiments of the disclosure has been presented only for the purposes of illustration and description and is not intended to be exhaustive or to limit the disclosure to the precise forms disclosed. Many modifications and deviations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. An optical sensing module, comprising:
   a light emitter for emitting a sensing light with a spectrum covering an infrared wavelength range; and
   a photodiode unit, including:
   a first photodiode for sensing a first wavelength light, the first photodiode is connected to a first signal converter and;
   a second photodiode for sensing a second wavelength light, the second photodiode is connected to a second signal converter; and
   a third photodiode for sensing a third wavelength light, the third photodiode is connected to a third signal converter;
   wherein the optical sensing module implements a proximity sensor by operations of the second photodiode and the third photodiode, and the optical sensing module implements a biometric sensor by operations of the first photodiode, the second photodiode, and the third photodiode.

2. The optical sensing module according to claim 1, wherein the first photodiode, the second photodiode, and the third photodiode are silicon photodiodes that include filter materials for different wavelength bands.

3. The optical sensing module according to claim 2, wherein a sensing area of at least one of the first photodiode and the third photodiode is configured to be larger than a sensing area of the second photodiode.

4. The optical sensing module according to claim 1, wherein the light emitter is a wide spectrum infrared light emitter to emit the sensing light with the spectrum covering a wavelength range from 800 nm to 1100 nm.

5. The optical sensing module according to claim 1, wherein a wavelength of the first wavelength light is between 870 nm and 910 nm, a wavelength of the second wavelength light is between 950 nm and 990 nm, and a wavelength of the third wavelength light is between 1030 nm and 1070 nm.

6. The optical sensing module according to claim 1, wherein the photodiode unit further includes one or more signal-regulating circuits.

7. An optical sensing system, comprising:
a control unit; and
an optical sensing module, electrically connected with the control unit, including a light emitter and a photodiode unit, wherein the photodiode unit includes a first photodiode, a second photodiode and a third photodiode; wherein the control unit drives the light emitter to emit a sensing light with a spectrum covering an infrared wavelength range and processes a sensing value generated by the photodiode unit when sensing the light reflected by an object; and the optical sensing module implements a proximity sensor by operations of the second photodiode and the third photodiode, and the optical sensing module implements a biometric sensor by operations of the first photodiode, the second photodiode, and the third photodiode.

8. The optical sensing system according to claim 7, wherein the first photodiode is connected to a first signal converter and used for generating a first sensing value by sensing a first wavelength light; the second photodiode is connected to a second signal converter and used for generating a second sensing value by sensing a second wavelength light; and the third photodiode is connected to a third signal converter and used for generating a third sensing value by sensing a third wavelength light; and wherein the first sensing value, the second sensing value and the third sensing value are converted into a first digital signal, a second digital signal, and a third digital signal by a first signal converter, a second signal converter and a third signal converter respectively.

9. The optical sensing system according to claim 8, wherein, when a sum of the second digital signal and the third digital signal is larger than or equal to a threshold, the proximity sensor determines if an object is proximal to the optical sensing module.

10. The optical sensing system according to claim 8, wherein, when both the first digital signal generated by the first signal converter and the third digital signal generated by the third signal converter are larger than the second digital signal generated by the second signal converter, the biometric sensor determines if a surface of an object is a human skin.

11. The optical sensing system according to claim 8, wherein, when a magnitude of the first digital signal is 1.1 to 2 times a magnitude of the second digital signal, and a magnitude of the third digital signal is 1.1 to 2 times the magnitude of the second digital signal, the object is determined as the human skin.

12. A method for operating an optical sensing system, comprising:
emitting a sensing light from a light emitter to an object, wherein the sensing light has a spectrum covering an infrared wavelength range;
receiving a reflected sensing light by a photodiode unit, wherein the photodiode unit includes a first photodiode for sensing a first wavelength light and generating a first sensing value, a second photodiode for sensing a second wavelength light and generating a second sensing value, and a third photodiode for sensing a third wavelength light and generating three sensing values;
converting the first sensing value, the second sensing value and the third sensing value into a first digital signal, a second digital signal, and a third digital signal by a first signal converter, a second signal converter and a third signal converter respectively;
determining the proximity of the object by the second digital signal and the third digital signal; and
determining whether or not a surface of the object is a human skin by the first digital signal, the second digital signal, and the third digital signal that are respectively converted from the three sensing values generated by the photodiode unit that implements a biometric sensor.

13. The method according to claim 12, wherein one or more signal-regulating circuits drives the first signal converter, the second signal converter, and the third signal converter to respectively adopt different gains.

14. The method according to claim 12, wherein a sensing area of at least one of the first photodiode and the third photodiode is larger than a sensing area of the second photodiode.

15. The method according to claim 12, wherein the first photodiode, the second photodiode, and the third photodiode are silicon photodiodes with different filter materials for different wavelength bands.

16. The method according to claim 15, wherein a wavelength of the first wavelength light is between 870 nm and 910 nm, a wavelength of the second wavelength light is between 950 nm and 990 nm, and a wavelength of the third wavelength light is between 1030 nm and 1070 nm.

17. The method according to claim 12, wherein the proximity is confirmed when a sum of second digital signal and the third digital signal is larger than a threshold.

18. The method according to claim 12, wherein the surface of human skin is confirmed when both the first digital signal and the third digital signal are larger than the second digital signal.

19. The method according to claim 12, wherein the surface of human skin is confirmed when a magnitude of the first digital signal is 1.1 to 2 times a magnitude of the second digital signal, and a magnitude of the third digital signal is 1.1 to 2 times the magnitude of the second digital signal.

* * * * *